US008397554B2

(12) United States Patent
Wargo et al.

(10) Patent No.: US 8,397,554 B2
(45) Date of Patent: Mar. 19, 2013

(54) METHOD OF TESTING SOFTNESS ATTRIBUTES OF PAPER TOWEL PRODUCTS

(75) Inventors: Courtney Lynn Wargo, West Chester, OH (US); Jeffrey Glen Sheehan, Cincinnati, OH (US); Christopher Clayton Dixon, Loveland, OH (US); Mark Phillip Wiley, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 205 days.

(21) Appl. No.: 13/010,825

(22) Filed: Jan. 21, 2011

(65) Prior Publication Data
US 2011/0179857 A1    Jul. 28, 2011

Related U.S. Application Data

(60) Provisional application No. 61/297,329, filed on Jan. 22, 2010.

(51) Int. Cl.
*G01N 3/00* (2006.01)
*G01N 3/08* (2006.01)

(52) U.S. Cl. ............................................. 73/78; 73/821
(58) Field of Classification Search ............... 73/78, 821
See application file for complete search history.

(56) References Cited

U.S. PATENT DOCUMENTS

| | | | |
|---|---|---|---|
| 5,633,453 A * | 5/1997 | Johnson ............................. 73/38 |
| 5,675,079 A * | 10/1997 | Gilman et al. .............. 73/117.01 |
| 5,691,919 A | 11/1997 | Gemmell et al. |
| 5,832,817 A * | 11/1998 | Bignell ........................... 100/51 |
| 5,878,381 A | 3/1999 | Gemmell et al. |
| 5,902,936 A * | 5/1999 | Serra-Tosio et al. ............ 73/851 |
| 6,378,386 B1 | 4/2002 | Schroder et al. |
| 7,062,983 B2 * | 6/2006 | Anderson et al. ............ 73/866.4 |
| 7,621,187 B2 * | 11/2009 | Chalmers ........................ 73/847 |
| 2002/0168622 A1 | 11/2002 | Cates et al. |
| 2006/0105316 A1 | 5/2006 | Harkin |
| 2007/0117084 A1 | 5/2007 | Julian et al. |

OTHER PUBLICATIONS

"The Egg Drop"; Akron Global Polymer Academy at the University of Akron; K-12 Science Education; National Science Standards; http://www.agpa.uakron.edu/k12/national_standrads/egg6d.htm, Jan. 19, 2010.
"Courtney's Egg Container"; http://www.nuuanu.k12.hi.us/nuuanuweb/06-07/5/hlegg/Courtney_Bonilla.html, Jan. 19, 2010.
"Gel-Ride™ Saddle Pads"; http://www.gelride.com/Egg_drop_test.htm, Jan. 19, 2010.

* cited by examiner

*Primary Examiner* — Lisa Caputo
*Assistant Examiner* — Jamel Williams
(74) *Attorney, Agent, or Firm* — Roddy M. Bullock; Betty J. Zea

(57) ABSTRACT

An apparatus for conducting demonstrations of the softness properties of consumer products and other materials, plus a method for conducting such demonstrations, is provided. A sample of paper towels, toilet tissue, or facial tissue, or other consumer products is placed in the apparatus. The apparatus drops an egg or other fragile object onto the sample, or the egg may be dropped from an operator's hand into the apparatus and onto the sample. By displaying the egg or fragile object as it either lands safely on a sample or is destroyed on impact, the operator can visually demonstrate to an average consumer either the softness properties of the sample, or the lack thereof. A method of preparing samples in a consistent manner is also provided to ensure that results are as fair, uniform and repeatable as possible.

16 Claims, 6 Drawing Sheets

METHOD OF TESTING SOFTNESS ATTRIBUTES OF PAPER TOWEL PRODUCTS

CROSS REFERENCE TO RELATED APPLICATION

This application claims the benefit of U.S. Provisional Application No. 61/297,329, filed Jan. 22, 2010.

FIELD OF THE INVENTION

This disclosure relates generally to an apparatus and associated method for demonstrating the softness qualities of paper towels and other consumer products.

BACKGROUND OF THE INVENTION

Market research has shown that "softness" is a property of paper-based consumer products, such as paper towels, paper napkins, bathroom tissue, and the like, as well as some non-paper-based consumer products, which is important to consumers in selecting and determining the quality and desirability of such products. Therefore, it is advantageous to be able to demonstrate a consumer product's softness to the consumer, as a way of making the product more desirable.

Consumer perception of softness is complex, composed of multiple vectors such as surface smoothness, fuzziness, scratchiness, cottony, flexibility, cushy, etc. There is no single test that quantifies overall softness. There are existing methods for scientifically quantifying and demonstrating certain components of softness. One such method for testing a given product's cushy softness is to use a compressive testing machine, such as the Vantage Compression Tester, available from Thwing-Albert Instrument Company of West Berlin, N.J. Such a machine will apply an increasing force to the surface of a paper towel or other test sample placed between two metal surfaces, and measure the caliper of the sheet as the amount of force applied to the sheet is increased. Caliper is the distance between the stationary platform on which the sample is placed and the foot used by the instrument to apply force to the sample.

The amount of each successive weight applied and the corresponding amount of compression of the towel (as measured by the test equipment's caliper) may be plotted on a graph, as illustrated in FIG. 1. The data points shown in FIG. 1 are plotted with the compressive pressure applied to the test sample (in grams/sq. in.) plotted linearly on the horizontal (x) axis, and the caliper reading (in mils) plotted linearly on the vertical (y) axis, with a smaller caliper reading indicating a narrower gap between the two metal testing surfaces. This data may be used to calculate the compressibility of the material tested by re-plotting the data with the caliper reading plotted linearly on the vertical (y) axis and the weight applied plotted logarithmically on the horizontal (x) axis, as shown in FIG. 2. A linear regression of the data plotted in FIG. 2 is performed to reduce the data to a straight line. The magnitude of the slope of that line is indicative of the compressibility of the material. A high value of compressibility, as determined by this test process, is highly analogous to the more subjective "softness" quality of paper towels and other consumer products. Such softness has been identified as a desirable property in paper products during consumer product testing.

One significant drawback of using compressive testing equipment is that the results of scientific compressibility testing, while perhaps easily understood by one who is literate in the art of materials testing or in mathematics, may not be understood by the average consumer, who may not readily recognize how the quantitative results of scientific testing relate to the more subjective "soft" feeling of an actual paper towel or other consumer product. Therefore, a more dynamic method of demonstrating the softness of a consumer product, using easily understood methods and familiar test materials, is desirable. Ideally, this method would use the paper towel product in a manner easily understood and related to by consumers. Such a method could be filmed or photographed and then used in advertisements, or it could be carried out in the direct presence of consumers, as a live demonstration in a store or other public location.

SUMMARY OF THE INVENTION

The present disclosure includes a method for testing the cushy softness, or lack of cushy softness, of paper towels (or other consumer products) by placing a sample of the product, prepared and arranged according to a standardized method, onto a testing surface of a testing apparatus of the present disclosure. In use, a single fragile object, such as a burstable pouch, paint ball, or most preferably, a chicken egg, is dropped from a predetermined height onto the sample, which may be arranged as a test substrate including a stack of quarter-folded paper towel sheets. When the fragile object strikes the test substrate, i.e. the paper towel stack, it either breaks onto the test substrate or lands intact. When the testing apparatus is properly calibrated and used, the breaking of the fragile object upon impact of striking the test substrate is indicative of a lack of cushy softness of the paper towel sheets, whereas a fragile object landing intact on the test substrate is indicative of the paper towel sheets exhibiting a presence of cushy softness. A clear plastic tube may be used to guide the fragile object to the stack of towels below, so as to isolate the fall of the fragile object from wind or other outside influences, while still allowing spectators to see the fragile object falling. A net arranged around the test substrate prevents the fragile object from rolling or bouncing off the stack and breaking once it lands. The apparatus is designed, and the method is performed, such that the entire test is visible to spectators, who can observe the test and can understand how the test results demonstrate the cushy softness of the paper towels, even without understanding the scientific principles and data analysis utilized in prior-art testing methods.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
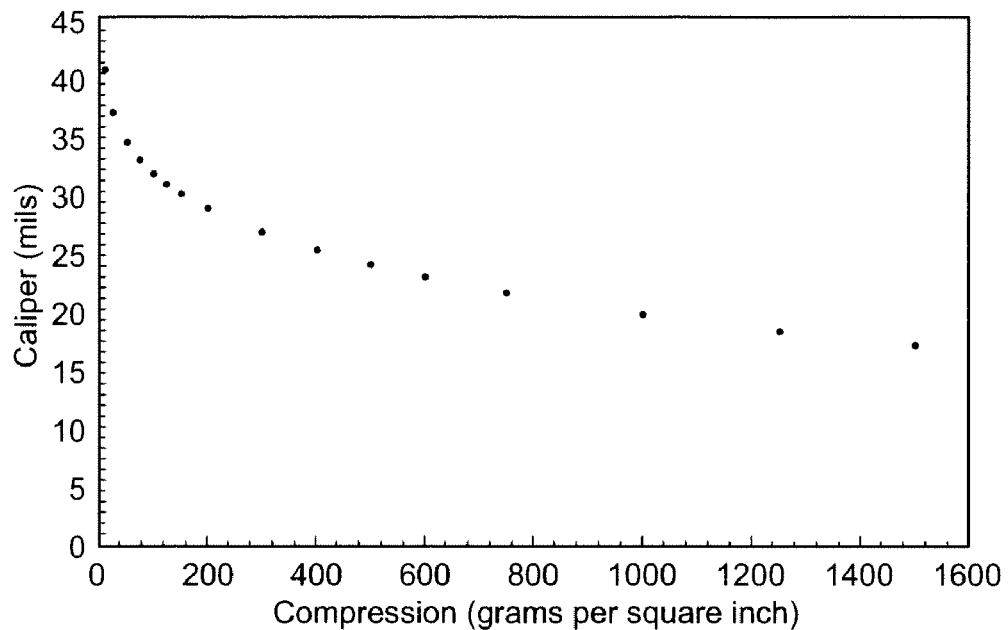
FIG. 1 is an exemplary plot of a conventional compression test, with caliper reading (in mils) plotted on the vertical (y) axis in a linear scale, and compression (in grams/sq. in.) plotted along the horizontal (x) axis in a linear scale.
Figure 2:
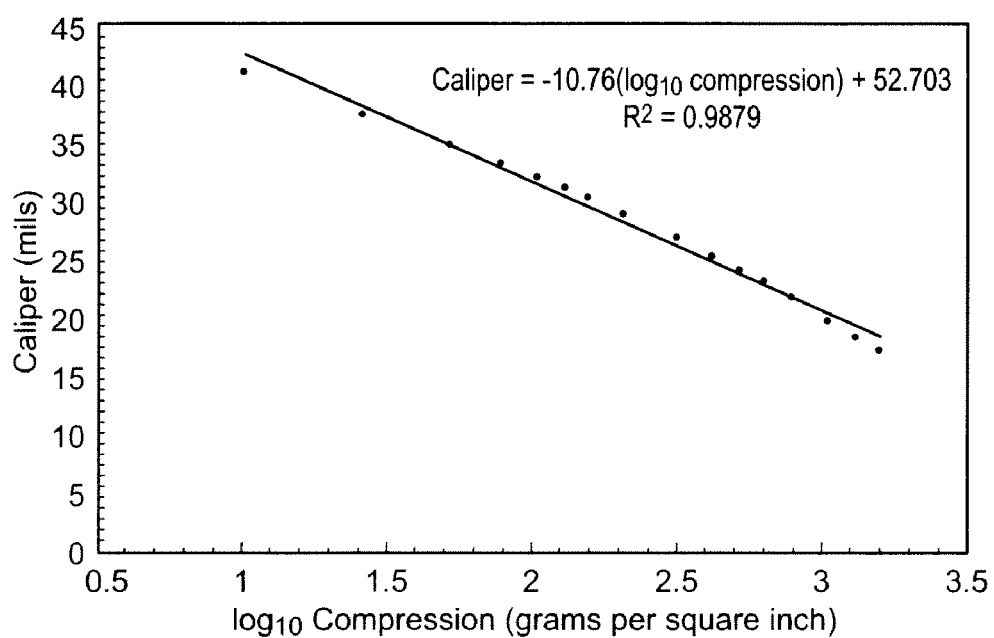
FIG. 2 is an exemplary plot of a conventional compression test, with caliper reading (in mils) plotted on the vertical (y) axis in a linear scale, and compression (in grams/sq. in.) plotted along the horizontal (x) axis in a logarithmic scale.
Figure 3:
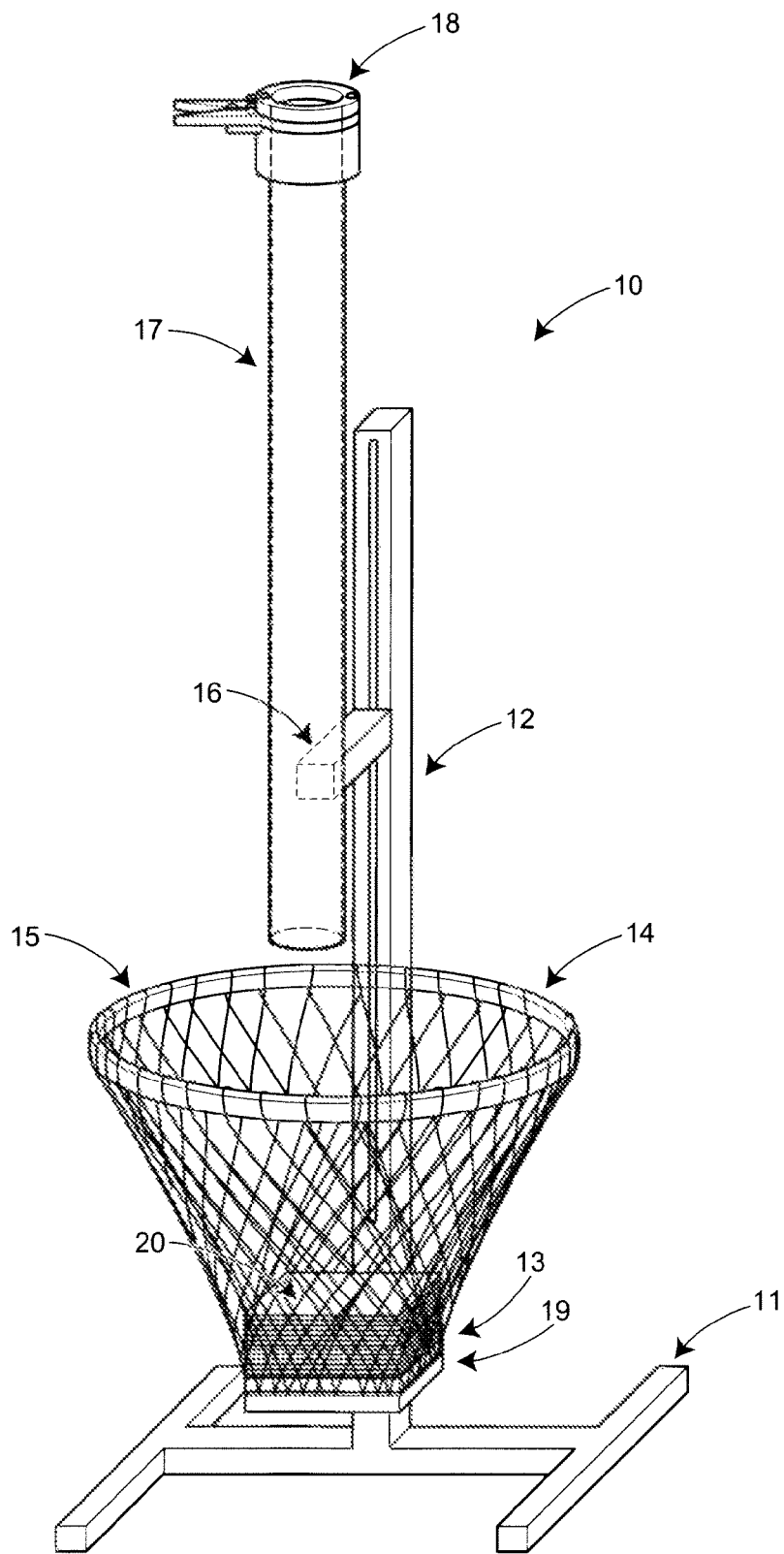
FIG. 3 is a perspective view of a demonstration apparatus of the present disclosure.

A testing apparatus 10 of the present disclosure is illustrated in FIG. 3. The testing apparatus 10 includes a base 11 which is of sufficient lateral dimensions to provide stability to the testing apparatus 10 and maintain the testing apparatus 10 in the desired orientation during use. A riser 12 extends vertically from the base to provide structural support to other components. Mounted to the riser 12 above the base 11 is a testing surface 13. The testing surface 13 is oriented in the horizontal plane, and provides a rigid surface upon which the material to be tested by the testing apparatus 10, which material is referred to herein as a test substrate 20, may be placed. Mounted to the riser 12 above the testing surface 13 is a net support 14. The net support 14 may be a rigid ring oriented in a plane parallel to the testing surface 13. Extending from the net support 14 down to the underside of the testing surface 13 is a safety net 15. The safety net 15 is held against the underside of the testing surface 13 by a secondary plate 19. The secondary plate 19 is substantially of the same size and shape as the testing platform 13 and affixes to the underside of testing platform 13, with the bottom of safety net 15 held between the testing platform 13 and the secondary plate 19. Secondary plate 19 prevents the safety net 15 from separating from the perimeter of test platform 13 when safety net 15 is placed under stress from within the net.

A guide tube support 16 is preferably mounted to the riser 12 and receives a guide tube 17. The guide tube support 16 may be adjusted up and down relative to the riser 12 and locked into any desired position along the riser 12. The guide tube 17 is preferably constructed of clear plastic. It is affixed to the guide tube support 16 such that the guide tube 17 is vertical, and its centerline passes through the center of testing surface 13. Both the top and bottom ends of the guide tube 17 are open. A fragile object release mechanism 18 may be affixed to the top of the guide tube 17 such that, when activated, it releases a fragile object, preferably an egg, and most preferably a raw grade A chicken egg, which then falls through the center of guide tube 17 onto the testing surface 13 below. Alternatively, no fragile object release mechanism 18 may be used, and the fragile object may be manually held at a predetermined height above the testing surface and released. However, the fragile object release mechanism 18 is preferred, as it mitigates influences, whether intended or accidental, that a human hand may impart to the fragile object upon manual release. While the fragile object may be a chicken egg, the fragile object may take other forms that will provide a visual indication of fracture upon impact, such as a burstable pouch or a paint ball.

By adjusting the height of the guide tube support 16 relative to the riser 12, a predetermined height of the fragile object release mechanism 18 may be determined, such that a fragile object, such as a raw chicken egg, will break upon impact with the test substrate 20 when dropped from that height onto products that do not possess properties consistent with cushy softness, and will not break upon impact with the test substrate 20 when dropped from that height onto products that do possess properties consistent with cushy softness.

The testing surface 13 is a horizontal surface, supported above the base 11 by the riser 12, which provides a place for the testing substrate 20 to rest. The testing surface 13 is constructed of a rigid material, such as aluminum, and must be mounted firmly to the riser 12. If the testing surface 13 is not firmly mounted during a test or is not constructed from a sufficiently rigid material, then the testing surface 13 may deflect or shift during the test, adversely affecting the reliability of the test results. Such deflection or shifting could result in irregular or inaccurate demonstration results.

Figure 4:
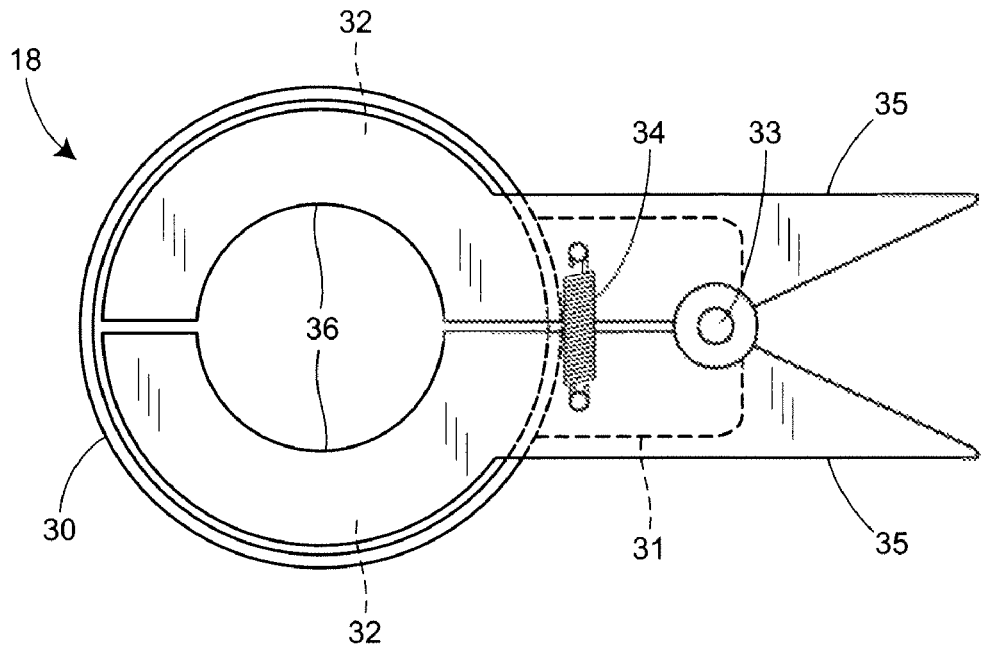
FIG. 4 is a top plan of a fragile object release mechanism of the demonstration apparatus of FIG. 3, illustrating the fragile object release mechanism in a closed position.
Figure 5:
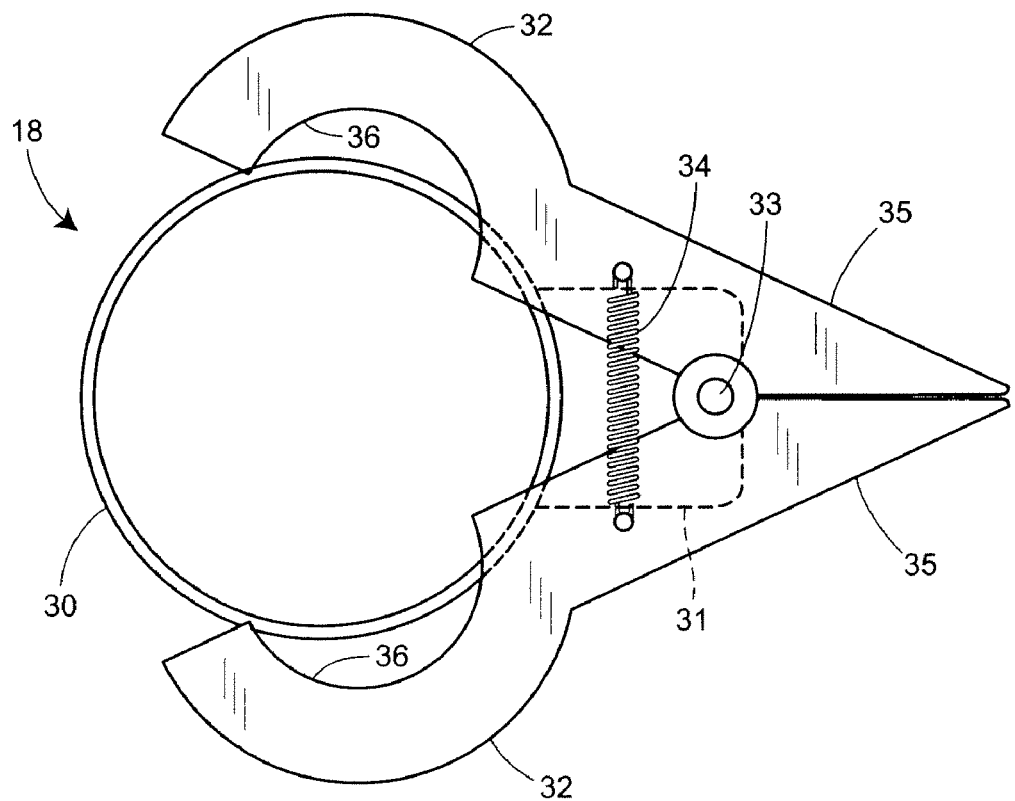
FIG. 5 is a top plan of a fragile object release mechanism of FIG. 4 in an open position.
Figure 6:
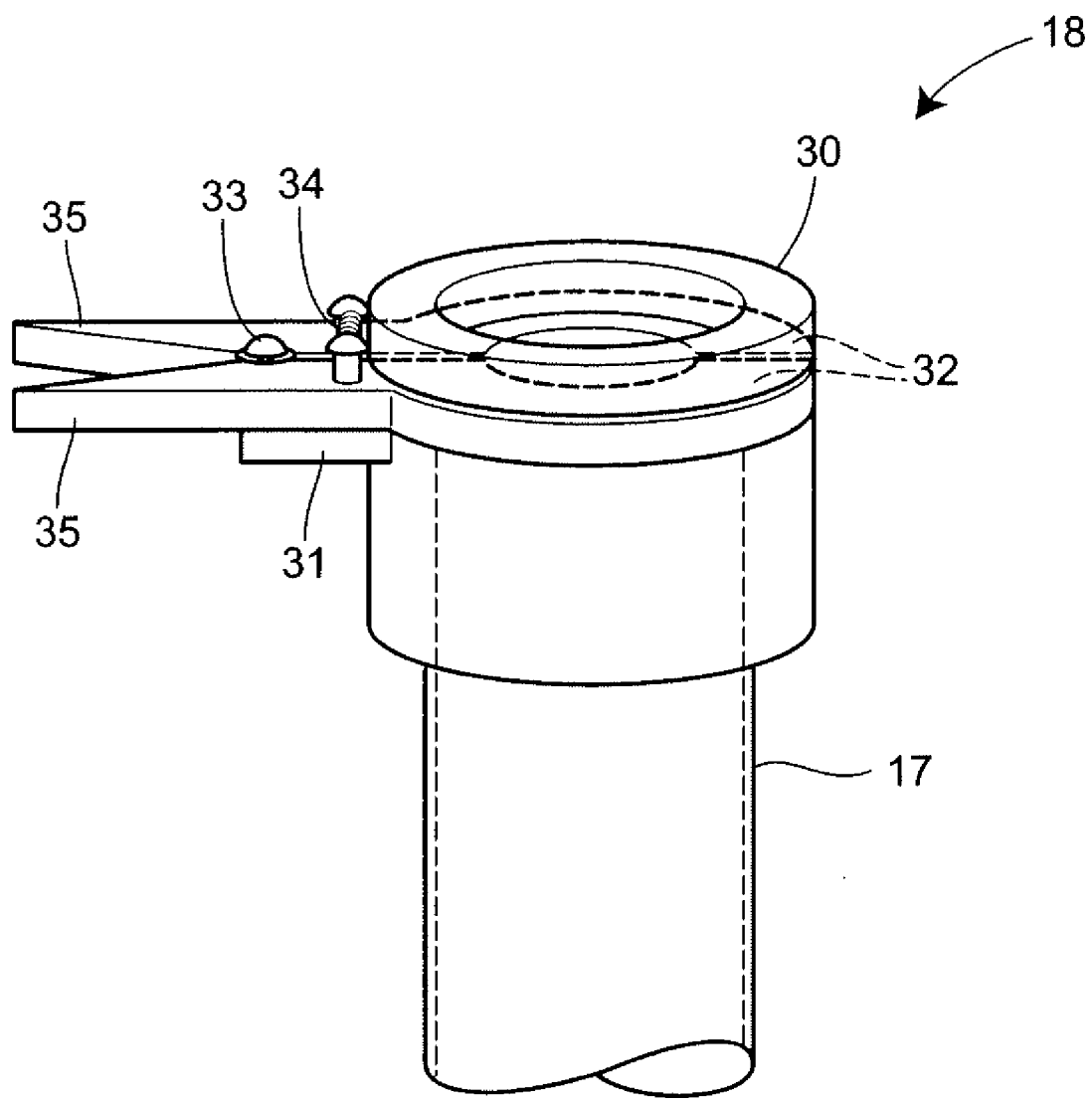
FIG. 6 is a perspective view of a fragile object release mechanism.

The fragile object release mechanism 18 is illustrated in FIG. 4. The fragile object release mechanism 18 has a body 30 preferably made of plastic. The body 30 is cylindrical and hollow, with the top and bottom of the body 30 open such that a fragile object may pass through. The axis of the cylindrical body 30 is shared with that of the guide tube 17 when the fragile object release mechanism 18 is mounted atop the guide tube 17. The body 30 has a tab 31 mounted parallel to the ground, extending from its side. Two clamshell-shaped jaw members 32, hereafter referred to as "clamshells," also of plastic, are mounted atop the tab 31 at a common pivot point 33. The clamshells 32 are free to rotate in the horizontal plane about the pivot point 33. FIGS. 4 and 5 illustrate the fragile object release mechanism 18 with the clamshells 32 in the closed and open positions, respectively. A handle 35 extends horizontally from an end of a generally C-shaped portion of each clamshell 32, extending away from the body 30. The pivot point 33 may be provided by a screw extending through an overlapping region of the two handles 35. A spring 34, provided between the two clamshells 32, biases the clamshells 32 toward the closed position.

The fragile object release mechanism 18 is used to release the fragile object into the guide tube 17 in a controlled manner, and may result in more accurate and uniform demonstration results than in-hand release of the fragile object. Inner concave edges 36 of clamshells 32 cooperate with one another to define an opening that is contoured to support the fragile object when the clamshells 32 are in the closed position. (In FIGS. 4 and 5, the inner concave edges 36 of the clamshells 32 define an opening that is substantially circular in shape, suitable for supporting a chicken egg.) An egg or other fragile object may be placed such that part of the fragile object protrudes through the opening between clamshells 32 and the bulk of the fragile object rests upon the inner concave edges 36 of clamshells 32. Spring 34 is of sufficient stiffness that the weight of the egg alone is insufficient to open clamshells 32. To initiate a demonstration, an operator places his or her fingers on the outer edges of handles 35 and rapidly draws handles 35 toward one another. Finger pressure exerted on the handles 35 overcomes the restoring force of spring 34 and moves the clamshells 32 to the open position. As the inner concave edges 36 of clamshells 32 move apart, the fragile object is free to fall into the guide tube 17. Releasing the fragile object via the fragile object release mechanism 18 helps to maintain the fragile object at (or close to) the center axis of guide tube 17 as it is initially dropped, and helps to eliminate vertical forces, rotation, and other undesirable motions which may be inadvertently imparted upon the fragile object by manual, in-hand release.

The test substrate 20 is a sample of the material whose cushy softness is being demonstrated, such as paper towels, toilet tissue, facial tissue, or other consumer products. The test substrate 20 is prepared by the tester prior to conducting the demonstration. The number of layers, size, and other properties of such materials may be determined by the tester as desired for the particular materials being tested. Because the testing method may be employed to demonstrate the cushy softness properties of several different materials, including but not limited to paper towels, toilet tissue, facial tissue, napkins, cloth, packing foam, bubble wrap, and pillows, the test substrate 20 may be constructed using a method customized to the properties of the exact material being tested.

Note that regardless of what materials are being tested, it is desirable for the uniformity, repeatability, and trustworthiness of the test results that the testing substrate 20 be prepared in an identical manner for each repetition of the demonstration. An example of such a procedure is illustrated in FIGS. 7-10, which illustrate a procedure for preparing a test substrate 20 from two-ply paper towels featuring a design embossed into one of the plies, such as Bounty Extra Soft™ brand paper towels.

A predetermined number of paper towel sheets are taken from a roll of paper towels. The first two and last two paper towels on a roll are not usable for the testing substrate, since they may contain glue which affects the properties of the paper towel.

Figure 7:
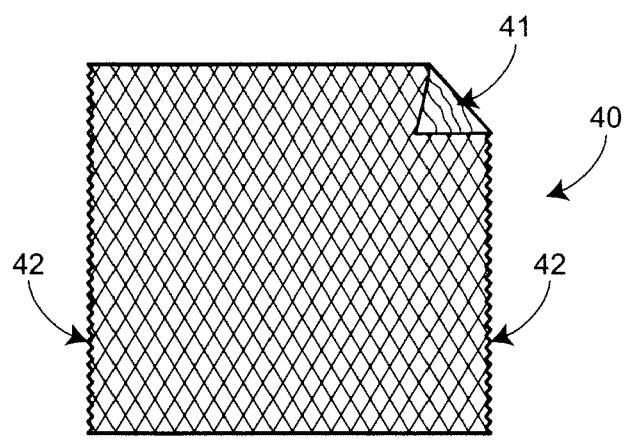
FIG. 7 is a top plan of a paper towel sheet used to create a test substrate.
Figure 8:
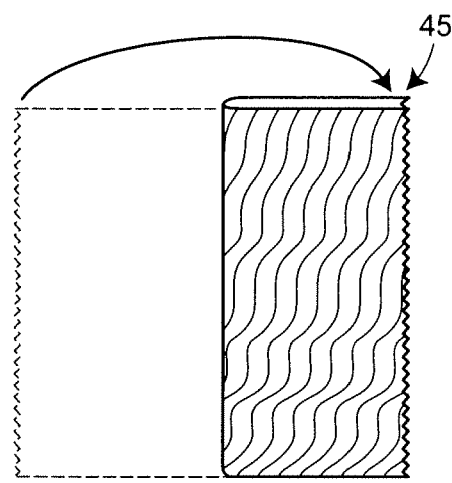
FIG. 8 is a top plan of a paper towel sheet that has been half-folded.
Figure 9:
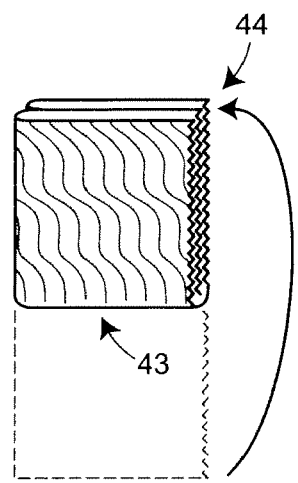
FIG. 9 is a top plan of a paper towel sheet that has been quarter-folded.

One by one, the paper towel sheets are quarter-folded. A single two-ply paper towel sheet 40 is placed on a table or other flat surface in front of the person preparing the test substrate 20, with the design-embossed ply 41 facing down and the perforated edges 42 on the left and right, as illustrated in FIG. 7. The paper towel sheet 40 is then half-folded by lifting the left perforated edge of the towel and folding it over to meet the right perforated edge, as pictured in FIG. 8. Then, the half-folded paper towel sheet 45 is quarter-folded by lifting the bottom edge of the half-folded paper towel sheet 40 and the towel is folded so that the bottom edge of the half-folded paper towel sheet 45 is even with the top edge, as depicted in FIG. 9. The bottom edge of the resulting quarter-folded paper towel sheet 44 is the closed edge 43.

Figure 10:
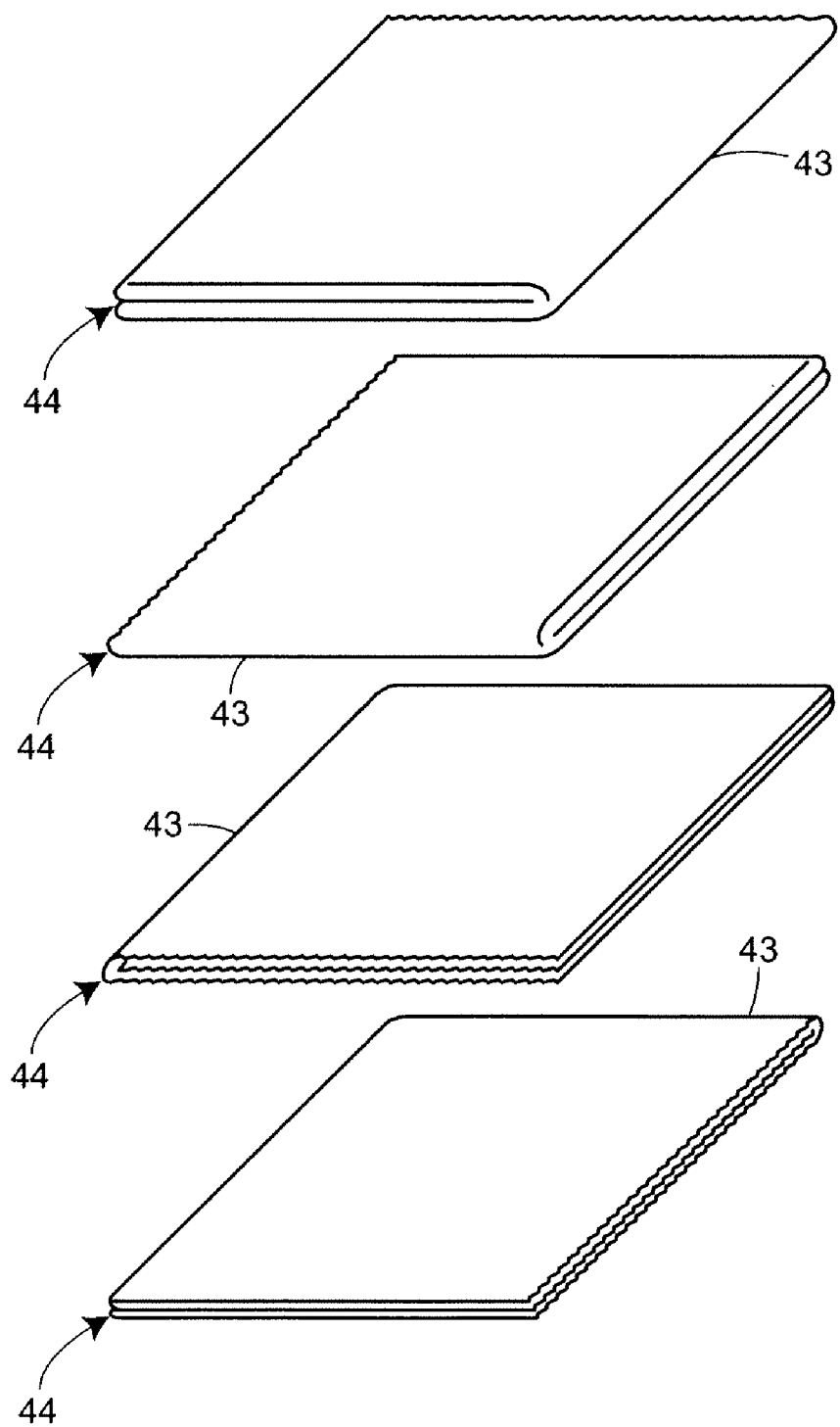
FIG. 10 is an exploded perspective view of four quarter-folded paper towel sheets being assembled into a test substrate.

Multiple quarter-folded paper towel sheets 44 may be stacked to form a single test substrate 20, as shown in FIG. 10. The stack starts with a single quarter-folded paper towel sheet 44 on the table. Additional quarter-folded paper towel sheets 44 are added on top of the first, with the closed edge 43 of each additional quarter-folded paper towel sheet 44 rotated 90 degrees from the quarter-folded paper towel sheet 44 beneath it. The rotation of each subsequent quarter-folded paper towel sheet 44 added to the stack helps to keep the stack vertical as additional quarter-folded paper towel sheets 44 are added to the stack; when quarter-folded paper towel sheets 44 are added to the stack with the closed edge 43 of each quarter-folded paper towel sheet 44 on the same side of the stack, the stack may curve to one side as additional quarter-folded paper towel sheets 44 are added. Once the predetermined number of paper towel sheets 40 have been quarter-folded and stacked as described, the stack forms a test substrate 20 which may be placed on the testing surface 13 in preparation for a demonstration. A test substrate 20 should not be used for more than one demonstration, as the impact of the falling egg or other fragile object upon the test substrate 20 during the first demonstration may affect the properties of the test substrate 20 during subsequent demonstrations. While folding each of the paper towel sheets 40 into quarters, the preparer of the test substrate 20 should exercise care not to exert excessive pressure on the paper towel sheets 40, such as by pressing down on the paper towel sheets 40, as such excess pressure can tend to flatten embossments on the paper towel sheets 40 or otherwise adversely affect results of the test. Use of excessive pressure is to be avoided even when folding paper towel sheets 40 lacking embossments, as such excessive pressure could adversely influence the test results.

While the demonstration method is not intended to produce precise quantitative results, the method must be performed with some amount of particularity. This helps to maximize the repeatability of the test results, and ensure that the test is performed in a manner that appears fair and trustworthy to consumers.

Example

A testing apparatus was assembled that included an aluminum testing surface in the shape of a rectangular plate. The testing surface was secured to a riser. The riser was a vertically-oriented bar having an elongate channel along its length to facilitate clamping of objects to the riser. The riser was secured to a sturdy support stand to maintain its vertical orientation. A transparent plastic guide tube was also secured to the riser, with its longitudinal axis aligned parallel to the channel of the riser. A fragile object release mechanism was provided at the top of the transparent plastic guide tube.

The fragile object release mechanism included a pair of jaw members hingedly attached to one another by a screw, each of the jaw members including a generally C-shaped portion defining a clamshell-shaped jaw member, with the concave region of each of the two generally C-shaped portions facing one another, and a handle arm extending from one end of the clamshell-shaped jaw member. A spring was attached to both of the jaw members at a location along the handle arms, between a pivot point of the hinged attachment and the generally C-shaped portions, the spring biasing the generally C-shaped portions toward one another. When in a closed position, the concave regions of the two clamshell-shaped jaw members cooperate to define a circular opening having a circumference less than a maximum diameter of a large Grade A chicken egg.

The transparent plastic guide tube was mounted on the riser such that the clamshell-shaped jaw members were spaced approximately 68.5 inches (174 cm) from the testing surface. Netting was provided around the testing surface, suspended from a hoop secured approximately 10 inches (25.4 cm) above the testing surface, and extending underneath the test surface so as not to interfere with the testing surface. A secondary plate was provided under the testing surface to hold the netting taut.

A test substrate was prepared by folding each of six separate sheets of two-ply paper towel into quarters, and stacking the folded paper towel sheets, rotating each sheet one-quarter turn, or 90°, relative to the next-adjacent folded paper towel sheet of the stack. The paper towel sheets included embossing on a surface of one of the two plies. When folding each of the paper towel sheets into quarters, each of the paper towel sheets was folded so that the embossed surface of the paper towel sheet faced outward. This was accomplished by first placing each of the paper towel sheets on a table. Next, the paper towel sheet was oriented so that the perforations of the paper towel sheet faced left and right on the table, from the point of view of the preparer. Next, the paper towel sheet was folded in half, left to right, so that the perforations were in alignment with one another. Next, the paper towel sheet was folded in half again, top to bottom, so that the quarter-folded towel sheet had the emboss pattern visible and facing outward. When folding and stacking the sheets, the preparer was careful not to impart excessive pressure on the paper towel sheets, in order to minimize flattening of the embossments or otherwise altering the paper towel sheets in a manner that could adversely influence the test results.

The test substrate of six quarter-folded paper towel sheets was placed on the testing surface. With the clamshell-shaped jaw members in a closed position, a large-size Grade A raw chicken egg was inspected to confirm its shell was free of cracks, then placed so as to rest between the clamshell-shaped jaw members of the egg release mechanism. The handle arms of the egg release mechanism were then squeezed toward one another, causing the clamshell-shaped jaw members to move apart from one another and release the egg, upon which the egg dropped onto the test substrate, did not break, and was prevented by the netting from rolling or bouncing off the testing surface. The test was conducted sixty times, utilizing a new test substrate of six new sheets of two-ply Bounty Extra Soft™ brand paper towel and a new large-size Grade A raw chicken egg each time, and the egg remained intact upon the impact of striking the test substrate during 57 out of 60 repetitions of the test, or 95% of the time. The test was performed under the same conditions an additional sixty times utilizing a test substrate of six new sheets of a different brand of two-ply brand paper towel sheets embossed on one of the plies, and a new large-size Grade A raw chicken egg each time, and the egg broke upon the impact of striking the test substrate during 57 out of 60 repetitions of the test, or 95% of the time.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for testing the softness of a consumer product, comprising: a testing surface;
    a fragile object selected from a group of a chicken egg, a burstable pouch, and a paint ball, the fragile object initially disposed at a predetermined height above the testing surface; and
    a test substrate disposed on the testing surface, the test substrate constructed from the consumer product, and the fragile object being releasable from the predetermined distance above the testing surface to drop onto the test substrate.

2. The apparatus of claim 1, wherein the fragile object is a raw chicken egg.

3. The apparatus of claim 1, wherein the fragile object is initially disposed in a release mechanism mounted so as to hold the fragile object at the predetermined height above the testing surface.

4. The apparatus of claim 2, wherein the raw chicken egg is initially disposed in a release mechanism mounted so as to suspend the raw chicken egg at the predetermined height above the testing surface, and wherein the release mechanism includes a body and a pair of clamshells.

5. The apparatus of claim 4, the release mechanism further comprising a spring connected to each of the pair of clamshells.

6. The apparatus of claim 1, further comprising a safety net extending upward and outward from the testing surface.

7. The apparatus of claim 3, further comprising a guide tube, positioned above the testing surface and below the release mechanism.

8. A method for demonstrating whether or not a consumer product possesses properties consistent with softness, comprising:
    preparing a test substrate;
    placing the test substrate onto a testing surface;
    releasing a fragile object, the fragile object being selected from a group including a chicken egg, a burstable pouch, and a paint ball, from a predetermined height above the testing surface, said predetermined height selected such that the fragile object will break upon impact with the test substrate when dropped from that height onto products that do not possess properties consistent with softness and will not break upon impact with the test substrate when dropped from that height onto products that do possess properties consistent with softness, whereby the fragile object falls onto the test substrate.

9. The method of claim 8, wherein in releasing the fragile object, the fragile object is a chicken egg.

10. The method of claim 8, wherein in releasing the fragile object, a release mechanism is actuated.

11. The method of claim 8, wherein in releasing the fragile object, the fragile object is released manually.

12. The method of claim 8, wherein preparing the test substrate includes arranging one or more paper towel sheets, toilet tissue sheets or facial tissue sheets.

13. The method of claim 12, wherein the test substrate is one or more paper towel sheets, each of the one or more paper towel sheets includes a plurality of plies.

14. The method of claim 13, wherein preparing the test substrate includes folding each of the of one or more paper towel sheets into quarters.

15. The method of claim 14, in which the quarter-folded paper towel sheets comprising the test substrate are stacked with the closed edge rotated ninety degrees from the quarter-folded paper towel sheet below it.

16. The method of claim 14, wherein each of the one or more paper towel sheets includes embossing on at least one surface thereof, and in folding each of the one or more paper towel sheets into quarters, folding each of the sheets such that an embossed surface of each of the paper towel sheets faces outward.

* * * * *